United States Patent [19]

Isoai et al.

[11] Patent Number: 5,548,062
[45] Date of Patent: Aug. 20, 1996

[54] TUMOR CELL INVASION-INHIBITING PEPTIDES, PEPTIDE COMPLEXES AND CANCER METASTASIS INHIBITORS

[75] Inventors: Atsushi Isoai, Yokohama; Yuko Hama, Musashino; Hiromichi Kumagai, Yokohama, all of Japan

[73] Assignee: Asahi Glass Company Ltd., Tokyo, Japan

[21] Appl. No.: 157,437

[22] Filed: Nov. 26, 1993

Related U.S. Application Data

[63] Continuation of Ser. No. 916,118, filed as PCT/JP91/01648, Nov. 29, 1991, abandoned.

[30] Foreign Application Priority Data

| Nov. 30, 1990 | [JP] | Japan | 2-330612 |
| Feb. 5, 1991 | [JP] | Japan | 3-035260 |
| Mar. 29, 1991 | [JP] | Japan | 3-091305 |
| Mar. 29, 1991 | [JP] | Japan | 3-091306 |

[51] Int. Cl.$^6$ .................. A61K 38/00; A61K 38/04; C07K 5/00; C07K 7/00
[52] U.S. Cl. .................. 530/326; 530/327; 530/328; 530/329; 530/345
[58] Field of Search ................... 530/330, 329, 530/328, 327, 326, 345; 514/13, 14, 15, 16, 17

[56] References Cited

U.S. PATENT DOCUMENTS

| 5,082,926 | 1/1992 | Chalberg et al. | 530/326 |
| 5,092,885 | 3/1992 | Yamada et al. | 623/11 |
| 5,120,828 | 6/1992 | Charonis | 530/326 |
| 5,175,251 | 12/1992 | Johnson et al. | 530/324 |
| 5,190,920 | 3/1993 | Eyal et al. | 514/17 |
| 5,231,082 | 7/1993 | Schasteen . | |

FOREIGN PATENT DOCUMENTS

| 0332912 | 9/1989 | European Pat. Off. . |
| 0347931 | 12/1989 | European Pat. Off. . |
| 2550223 | 2/1985 | France . |
| WO90/05522 | 5/1990 | WIPO . |
| WO90/10228 | 9/1990 | WIPO . |

OTHER PUBLICATIONS

Isoai et al., Jpn. J. Cancer Res. Sep. 1990 (81) pp. 909–914.

*Primary Examiner*—Howard E. Schain
*Assistant Examiner*—A. M. Davenport
*Attorney, Agent, or Firm*—Oblon, Spivak, McClelland, Maier & Neustadt, P.C.

[57] ABSTRACT

The present invention is a peptide having from 5 to 20 amino acid residues having tumor cell invasion-inhibiting activities. As such a peptide, a peptide represented by any one of the formulas (1) to (13) is preferred among peptides.

Further, the present invention is a cancer metastasis inhibitor comprising the above peptide as an active ingredient.

Furthermore, the present invention is a peptide complex having a peptide having tumor cell invasion-inhibiting activities and a polymer derived from a vital body chemically bonded to each other. As such a peptide, a peptide represented by any one of the formulas (1) to (14) is preferred among peptides. As the polymer derived from a vital body, a protein such as albumin or globulin is preferred.

Still further, the present invention is a cancer metastasis inhibitor comprising the above peptide complex as an active ingredient.

9 Claims, 3 Drawing Sheets

5,548,062

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: unknown ( i i ) MOLECULE TYPE: peptide ( x i ) SEQUENCE DESCRIPTION: SEQ ID NO:1:

Ala  Glx  Lys  Ala  Glx  Gly
1                   5

( 2 ) INFORMATION FOR SEQ ID NO:2:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( x i ) SEQUENCE DESCRIPTION: SEQ ID NO:2:

Ala  Glx  Lys  Ala  Glx  Gly  Ala
1                   5

( 2 ) INFORMATION FOR SEQ ID NO:3:

( i ) SEQUENCE CHARACTERISTICS:

(A) LENGTH: 8 amino acids
(B) TYPE: amino acid
(D) TOPOLOGY: unknown (ii) MOLECULE TYPE: peptide (xi) SEQUENCE DESCRIPTION: SEQ ID NO:3:

Ala Glx Lys Ala Glx Gly Ala Gly
1               5

(2) INFORMATION FOR SEQ ID NO:4:

(i) SEQUENCE CHARACTERISTICS:
(A) LENGTH: 9 amino acids
(B) TYPE: amino acid
(D) TOPOLOGY: unknown (ii) MOLECULE TYPE: peptide (xi) SEQUENCE DESCRIPTION: SEQ ID NO:4:

Ala Glx Lys Ala Glx Gly Ala Gly Asx
1               5

(2) INFORMATION FOR SEQ ID NO:5:

(i) SEQUENCE CHARACTERISTICS:
(A) LENGTH: 10 amino acids
(B) TYPE: amino acid
(D) TOPOLOGY: unknown (ii) MOLECULE TYPE: peptide (xi) SEQUENCE DESCRIPTION: SEQ ID NO:5:

Ala Glx Lys Ala Glx Gly Ala Gly Asx Ala
1               5                   10

(2) INFORMATION FOR SEQ ID NO:6:

(i) SEQUENCE CHARACTERISTICS:
(A) LENGTH: 11 amino acids
(B) TYPE: amino acid
(D) TOPOLOGY: unknown (ii) MOLECULE TYPE: peptide (xi) SEQUENCE DESCRIPTION: SEQ ID NO:6:

Ala Glx Lys Ala Glx Gly Ala Gly Asx Ala Lys
1               5                   10

(2) INFORMATION FOR SEQ ID NO:7:

(i) SEQUENCE CHARACTERISTICS:
(A) LENGTH: 12 amino acids
(B) TYPE: amino acid
(D) TOPOLOGY: unknown (ii) MOLECULE TYPE: peptide (xi) SEQUENCE DESCRIPTION: SEQ ID NO:7:

Asx Ala Lys Thr Asx Glx Ala Glx Lys Ala Glx Gly
1               5                   10

(2) INFORMATION FOR SEQ ID NO:8:

(i) SEQUENCE CHARACTERISTICS:
(A) LENGTH: 11 amino acids
(B) TYPE: amino acid
(D) TOPOLOGY: unknown (ii) MOLECULE TYPE: peptide ( x i ) SEQUENCE DESCRIPTION: SEQ ID NO:8:

Ala Lys Thr Asx Glx Ala Glx Lys Ala Glx Gly
1               5                   10

( 2 ) INFORMATION FOR SEQ ID NO:9:

( i ) SEQUENCE CHARACTERISTICS:
( A ) LENGTH: 10 amino acids
( B ) TYPE: amino acid
( D ) TOPOLOGY: unknown ( i i ) MOLECULE TYPE: peptide ( x i ) SEQUENCE DESCRIPTION: SEQ ID NO:9:

Lys Thr Asx Glx Ala Glx Lys Ala Glx Gly
1           5                   10

( 2 ) INFORMATION FOR SEQ ID NO:10:

( i ) SEQUENCE CHARACTERISTICS:
( A ) LENGTH: 9 amino acids
( B ) TYPE: amino acid
( D ) TOPOLOGY: unknown ( i i ) MOLECULE TYPE: peptide ( x i ) SEQUENCE DESCRIPTION: SEQ ID NO:10:

Thr Asx Glx Ala Glx Lys Ala Glx Gly
1               5

( 2 ) INFORMATION FOR SEQ ID NO:11:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: peptide ( x i ) SEQUENCE DESCRIPTION: SEQ ID NO:11:

Asx Glx Ala Glx Lys Ala Glx Gly
1               5

( 2 ) INFORMATION FOR SEQ ID NO:12:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( x i ) SEQUENCE DESCRIPTION: SEQ ID NO:12:

Glx Ala Glx Lys Ala Glx Gly
1               5

( 2 ) INFORMATION FOR SEQ ID NO:13:

( i ) SEQUENCE CHARACTERISTICS:
( A ) LENGTH: 6 amino acids
( B ) TYPE: amino acid
( D ) TOPOLOGY: unknown ( i i ) MOLECULE TYPE: peptide ( x i ) SEQUENCE DESCRIPTION: SEQ ID NO:13:

Asx Glx Ala Glx Lys Ala
1               5

(2) INFORMATION FOR SEQ ID NO:14:

(i) SEQUENCE CHARACTERISTICS:
        (A) LENGTH: 21 amino acids
        (B) TYPE: amino acid
        (D) TOPOLOGY: unknown (ii) MOLECULE TYPE: peptide (xi) SEQUENCE DESCRIPTION: SEQ ID NO:14:

Ala Glu Asp Gly Asp Ala Lys Thr Asp Glx Ala Glx Lys Ala Glu Gly
1               5                   10                  15

Ala Gly Asp Ala Lys
            20

TUMOR CELL INVASION-INHIBITING PEPTIDES, PEPTIDE COMPLEXES AND CANCER METASTASIS INHIBITORS

This application is a Continuation of application Ser. No. 07/916,118, filed Sep. 2, 1992, abandoned, which was filed as International Application No. PCT/JP91/01648 on Nov. 29, 1991.

TECHNICAL FIELD

The present invention relates to novel peptides having tumor cell invasion-inhibiting activities, complexes of peptides having tumor cell invasion-inhibiting activities with polymers, and cancer metastasis inhibitors comprising them as active ingredients.

BACKGROUND ART

For the treatment of cancer, surgical therapy, radiation therapy and chemotherapy are mainly employed. However, no satisfactory therapeutic results have been obtained with respect to recurrence and metastasis of cancer. Most of anti-cancer drugs presently available are designed to kill tumor cells by impairing biosynthesis of nucleic acids or proteins. However, in their activities, such anti-cancer drugs do not distinguish normal cells from tumor cells. Accordingly, there has been a serious problem that side effects are likely to result due to their cytotoxicity against normal cells. Moreover, such anti-cancer drugs are designed to reduce the primary focus for the treatment. However, metastasis of tumor cells has been a problem in the treatment of cancer. Namely, tumor cells leave from the primary site and move to other organs and proliferate there, thus leading to poor prognosis. Accordingly, for the fundamental treatment of cancer, it is desired to develop an anti-cancer drug which exhibits effective inhibiting activities not only against proliferation of tumor cells but also against invasion and metastasis of tumor cells.

Many studies have been made on the mechanism of metastasis of cancer, and searches for anti-metastatic substances have been widely conducted. Tumor cells released from the primary focus, will enter into a blood vessel. Then, the cells will adhere to the vascular wall and then penetrate underneath the vascular endothelial cell layer, and they will destroy the extracellular matrix and invade into the parenchyma of the target organ. In this way, tumor cells are believed to metastasize (L. A. Liotta et al., lab. Invest., 49,636–649, (1983)). It is believed that for the development of a drug for metastasis of tumor cells, a substance should be developed which controls any one of the above-mentioned steps. For example, it may be a substance which inhibits adherence of the tumor cells to the extracellular matrix (e.g. N. J. Humphries et al., Science, 223, 467–470 (1986)), a substance which inhibits the penetration underneath the mesothelial cell layer or underneath the vascular endothelial cell layer (e.g. Isoai et al., Jpn. J. Cancer Res., 81, 909–914 (1990)) or a substance which inhibits the destruction of the extracellular matrix (e.g. R. M. Schultz et al., Cancer Res., 48, 5539–5545 (1988)).

DISCLOSURE OF THE INVENTION

Under these circumstances, the present inventors have conducted extensive researches for substances which inhibit invasion of tumor cells. In particular, they have studied for the improvement of the above-mentioned substance which inhibits invasion of tumor cells developed by the present inventors (the peptide represented by the amino acid sequence of the formula (14) given hereinafter) and for the improvement of the activities and stability thereof. As a result, they have found novel peptides having a less number of amino acid residues and have further found that when the peptides which inhibit invasion of tumor cells are supported on carriers, their activities will be improved, and their stability in a vital body will be improved.

The present invention is an invention relating to peptides having from 5 to 20 amino acid residues having tumor cell. invasion-inhibiting activities, such as peptides having any one of the amino acid sequences represented by the following formulas (1) to (13), and acid addition salts thereof.

As the peptides having from 5 to 20 amino acid residues having tumor cell invasion-inhibiting activities, peptides having any one of the amino acid sequences represented by the following formulas (1) to (13) are preferred:

(1) Ala-Glx-Lys-Ala-Glx-Gly (SEQ ID NO:1)
(2) Ala-Glx-Lys-Ala-Glx-Gly-Ala (SEQ ID NO:2)
(3) Ala-Glx-Lys-Ala-Glx-Gly-Ala-Gly (SEQ ID NO:3)
(4) Ala-Glx-Lys-Ala-Glx-Gly-Ala-Gly-Asx (SEQ ID NO:4)
(5) Ala-Glx-Lys-Ala-Glx-Gly-Ala-Gly-Asx-Ala (SEQ ID NO:5)
(6) Ala-Glx-Lys-Ala-Glx-Gly-Ala-Gly-Asx-Ala-Lys (SEQ ID NO:6)
(7) Asx-Ala-Lys-Thr-Asx-Glx-Ala-Glx-Lys-Ala-Glx-Gly (SEQ ID NO:7)
(8) Ala-Lys-Thr-Asx-Glx-Ala-Glx-Lys-Ala-Glx-Gly (SEQ ID NO:8)
(9) Lys-Thr-Asx-Glx-Ala-Glx-Lys-Ala-Glx-Gly (SEQ ID NO:9)
(10) Thr-Asx-Glx-Ala-Glx-Lys-Ala-Glx-Gly (SEQ ID NO:10)
(11) Asx-Glx-Ala-Glx-Lys-Ala-Glx-Gly (SEQ ID NO:11)
(12) Glx-Ala-Glx-Lys-Ala-Glx-Gly (SEQ ID NO:12)
(13) Asx-Glx-Ala-Glx-Lys-Ala (SEQ ID NO:13)
wherein Glx is Glu or Gln, and Asx is Asn or Asp.

The peptides having amino sequences of the above formulas (1) to (13) (hereinafter referred to as "the peptide of the formula (1)" to "the peptide of the formula (13)") have invasion-inhibiting activities and anti-metastastatic activities (hereinafter these activities will be generally referred to as invasion-inhibiting activities, unless otherwise specified) by themselves. These peptides have invasion-inhibiting activities, whereby they have effects for controlling metastasis of tumor cells. Thus, they are peptides useful as cancer metastasis inhibitors.

Further, the peptide which the present inventors have already reported in a literature, is a peptide having an amino acid sequence of the following formula (14) (hereinafter referred to as "the peptide of the formula (14)"):

(14) Ala-Glu-Asp-Gly-Asp-Ala-Lys-Thr-Asp-Glx-Ala-Glx-Lys-Ala-Glu-Gly-Ala-Gly-Asp-Ala-Lys (SEQ ID NO:14)
wherein Glx is Glu or Gln.

Further, the present invention is an invention relating to a peptide complex having a peptide having tumor cell invasion-inhibiting activities supported on a substantially non-toxic polymer carrier. As the peptide having tumor cell invasion-inhibiting activities, at least one peptide selected from the peptides of the above formulas (1) to (14) is preferred. As the substantially non-toxic polymer, a polymer derived from a vital body is preferred, and to support the peptide thereon is preferably to chemically bond the two. This peptide complex is useful as a cancer metastasis inhibitor like the above-mentioned peptides.

This peptide complex is superior to the corresponding single peptide from the aspects of improvement in the invasion-inhibiting activities and in the stability in the vital body.

As the polymer carrier in the present invention, various types may be employed. A polymer derived from a vital body is preferred as such a polymer carrier. However, it may be a synthetic polymer acceptable as a medicine or a synthetic polymer such as a synthetic protein. As the polymer derived from a vital body, a protein derived from a vital body is preferred. However, it is not limited to such a protein. For example, it may be a polysaccharide derived from a vital body. Preferred polymers derived from vital bodies other than the proteins derived from vital bodies, are chondroitin sulfate and hyaluronic acid.

The protein derived from a vital body may be of any type so long as it is practically useful. However, it is preferably the one which has a high stability in blood and which can readily be available in a large amount at a low cost. For example, as plasma components, prealbumin, albumin, α-globulin protein, β-globulin protein, immunoglobulin protein, antithronbin, complement protein, fibrinogen, fibronectin and collagen, may, for example, be mentioned. Further, it may be a pharmaceutically acceptable enzyme protein.

The protein is preferably the one derived from human, but it may be the one derived from other animal. Particularly preferred proteins derived from vital bodies are the above-mentioned albumins or globulins.

In the peptide-protein complex, the number of peptide molecules bonded per molecule of protein is at least one molecule, preferably from 1 to 10 molecules. As the chondroitin sulfate or the hyaluronic acid, various types may be employed. Particularly, a chondroitin sulfate or a hyaluronic acid which is free from presenting an adverse effect to a vital body, is used. As the chondroitin sulfate, not only a commercial product, but also various chondroitin sulfates extracted from vital bodies such as cartilages or connective tissues, may be employed. Likewise, as the hyaluronic acid, not only a commercial product but also various hyaluronic acids extracted from vital bodies such as crista galli, may be employed. There is no particular restriction as to the molecular weights of these two materials, but they preferably have molecular weights of at least a few tens thousands.

In a peptide-chondroitin sulfate or hyaluronic acid complex, the amount of the peptide bonded is not particularly limited, and the bonded amount may be adjusted as the case requires. For example, the amount of peptide bonded per 1 mg of the complex is usually from 1 to 1,000 μg, preferably from 10 to 500 μg, although the amount is not so limited.

The complex of the present invention is preferably the one having the peptide and the protein or the like chemically bonded. However, the bonding may be physical bonding such as adsorption. The mode of the chemical bonding may, for example, be a carbodiimide condensation method, a cyan bromide activation method (Axen & Ernback (1971) Eur. J. Biochem., 18, 351) or a covalent bond obtained by e.g. a rearrangement (Ugi) reaction with a proton Schiff base followed by the reaction with an isocyan compound (Axen et al., Acta Chem. Scand., 25, 1129 (1971)).

For the application of such a bonding method, it is possible to employ a method wherein a water-soluble carbodiimide useful for the condensation of a substance required to be reacted in an aqueous system, is used, or a method wherein a technique for the preparation of a fixed enzyme or an affinity chromato carrier is used which comprises chemical modification and activation of a polysaccharide, followed by bonding a protein, a peptide or the like to a polymer carrier.

In the present invention, a particularly preferred method for the above bonding is a carbodiimide condensation method. Carbodiimides to be used in this method include, for example, the following carbodiimides, but as the carbodiimides, water-soluble carbodiimides are particularly preferred:

Diethyl carbodiimide, diisopropyl carbodiimide, methylpropyl carbodiimide, dicyclohexyl carbodiimide, hexamethylene carbodiimide, heptamethylene carbodiimide, 1-ethyl-3-(3-dimethylaminopropyl) carbodiimide, 1-cyclohexyl-3-(2-morpholinoethyl) carbodiimide, metho-p-toluene sulfonate, 1-t-butyl-3-(3-dimethylaminopropyl) carbodiimide, diphenyl carbodiimide, 4,4'-dinitrodiphenyl carbodiimide, di-p-trycarbodiimide, and bis(trimethylsillyl) carbodiimide.

As a specific process for the preparation of the complex, a suitable process may be employed depending upon the above-mentioned various methods. For example, in the case of a condensation method by means of a water-soluble carbodiimide, it is possible to employ a process which comprises dissolving in an aqueous solvent, the protein and any one of the peptides of the formulas (1) to (13) in an amount of from 1 to 60 equivalent relative to the protein, adjusting the pH to a level of from 7.5 to 8.5 and adding and reacting a water-soluble carbodiimide in an amount of at least equal by weight to the protein. By this process, the peptide-protein complex of the present invention can readily be obtained. The obtained complex is preferably purified by e.g. dialysis, alcohol precipitation, gel permeation, ion exchange or reversed phase chromatography.

In the present invention, as a method for searching a tumor cell invasion-inhibiting substance, a system developed by Akedo et al. (Cancer Res., 46, 2416–2422, (1986)) or a system by Albini et al. (Cancer Res., 47, 3239–3245, (1987)) may, for example, be employed.

The method of Akedo et al. is a method which comprises adding highly invasive floating cells onto rat mesothelial cell sheet obtained by the first culture and measuring the number of tumor cells penetrated underneath the mesothelial cell sheet after the incubation for 20 to 40 hours.

The method of Albini et al. is a method of employing a transwell chamber (an improved model of a Boyden chamber) comprising two layers i.e. upper and lower layers of a polycarbonate filter with pores of 8 μm. In this method, a matrigel of 50 μm (manufactured by Collaborative Research, Inc.) is coated on the upper side of a filter and dried, and an extracellular matrix component such as fibronectin is put in the lower layer as a chemoattractant. Metastatic tumor cells are added to the upper layer, and after the incubation for 20 to 40 hours, the number of tumor cells migrated to the lower side of the filter is counted.

In the present invention, for the evaluation of cancer metastasis using an animal, an experimental lung metastasis system which is commonly employed, is used. Namely, metastatic tumor cells of e.g. B16 melanoma or Lewis lung cancer are injected in the lateral tail vein of a mouse, and at 14 to 21 days after the injection, the lung is extracted, and the number of metastatic foci observed on the lung surface is counted to evaluate the metastatic ability of tumor cells.

In this manner, the peptide of the formula (1) to the peptide of the formula (13) and the peptide complex prepared by chemically bonding the polymer derived from a vital body and at least one peptide selected from the peptide of the formula (1) to the peptide of the formula (14), according to the present invention, were confirmed to exhibit strong tumor cell invasion-inhibiting activities and anti-metastatic activities and thus confirmed to be expected to be useful as cancer metastasis inhibitors.

BEST MODE FOR CARRYING OUT THE INVENTION

Figure 1:
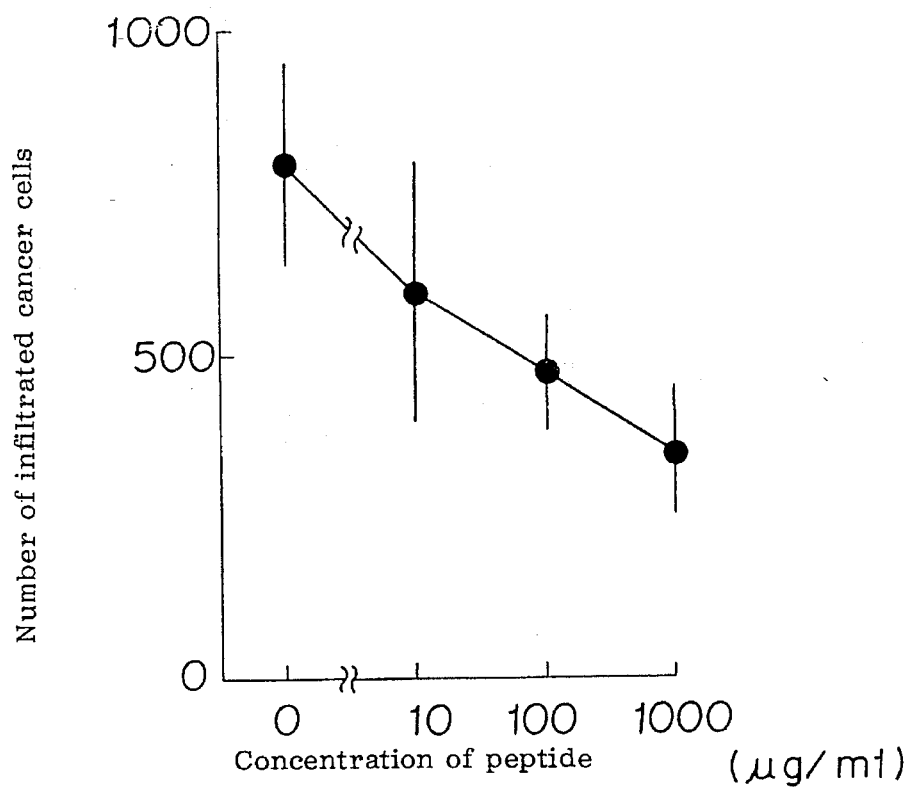
FIGS. 1 to 4 are graphs showing the results obtained by measuring the tumor cell invasion-inhibiting activities of the peptides and the peptide complex of the invention by the method of Albini et al. in Examples C and E-3 given hereinafter.

Now, the present invention will be described with reference to Examples. The abbreviations used to represent peptides have the following meanings.

Ala: Alanine, Glu: glutamic acid, Gln: glutamine, Glx: glutamic acid or glutamine, Asp: aspartic acid, Asn: asparagine, Asx: aspartic acid or asparagine, Gly: glycine, Lys: lysine, and Thr: threonien.

EXAMPLE A (Preparation of peptides)

Preparation of a peptide was conducted by the Merrifield' solid phase synthesis. Namely, the desired peptide was synthesized by an automatic synthesizer model 9050, manufactured by Milligen Company. Then, the prepared peptide was purified by high performance chromatography (HPLC) under the following purification conditions.

Column: C18 column, manufactured by Waters Company, Microbondas Fair C18 column (1.9×15 cm, particle diameter: 5 mm)

Eluate A: Water containing 0.1% trifluoroacetic acid

Eluate B: Acetonitrile containing 0.1% trifluoroacetic acid.

Flow rate: 10 ml/min Eluate B-was eluted under a linear concentration gradient from 0 to 40% over a period of from 0 to 30 minutes.

The eluted peptide was recovered and freeze-dried to obtain a purified peptide.

Then, a part of the obtained peptide was subjected to an amino acid analysis, and the amino acid composition (number of residues/mol) was determined.

Analysis: completely hydrolyzed in 6N hydrochloric acid at 110° C. for 24 hours under vacuum.

Further, using a reversed phase column, μBondasphere C18 column (0.39×15 cm), manufactured by Waters Company, an analysis was conducted by a HPLC system to measure the purity of the desired peptide.

By the above method, the following peptides were prepared and analyzed. Modifications of purification conditions, etc., and the results of the syntheses are shown below.

EXAMPLE A-1

Preparation of the peptide of the formula (7) (Asp-Ala-Lys-Thr-Asp-Gln-Ala-Glu-Lys-Ala-Glu-Gly; SEQ ID NO: 7)

Amino acid composition: Asx: 2.04, Ala: 2.93, Lys: 2.03, Thr: 0.89, Glx: 3.02, Gly:1.01

Purity of the peptide: at least 99%

EXAMPLE A-2

Preparation of the peptide of the formula (6) (Ala-Glu-Lys-Ala-Glu-Gly-Ala-Gly-Asp-Ala-Lys; SEQ ID NO: 6)

Amino acid composition: Asx: 0.98, Ala: 4.11, Lys: 1.97, Glx: 2.01, Gly: 2.08

Purity of the peptide: at least 99%

EXAMPLE A-3

Preparation of the peptide of the formula (13) (Asp-Gln-Ala-Glu-Lys-Ala SEQ ID NO: 13)

Modification: in the purification by HPLC, the linear concentration gradient of Eluate B was changed to from 0 to 30%.

Amino acid composition: Asx: 1.05, Ala: 1.99, Lys: 1.01, Glx: 2.01

Purity of the peptide: at least 99%

EXAMPLE A-4

Preparation of the peptide of the formula (9) (Lys-Thr-Asp-Gln-Ala-Glu-Lys-Ala-Glu-Gly SEQ ID NO: 9)

Amino acid composition: Asx: 0.98, Ala: 2.10, Lys: 2.01, Glx: 3.01, Gly: 1.01

Purity of the peptide: at least 99%

EXAMPLE B (Tumor cell invasion-inhibiting activities of the synthesized peptides)

With respect to the peptides prepared in Example A, the activities for inhibiting invasion of tumor cells were examined. The evaluation method was in accordance with the following Albini et al. method.

50 μg of matrigel (manufactured by Collaborative Research, Inc.) was coated on the upper side of a filter of Chemotaxicell (manufactured by Kurabo) divided into an upper layer and a lower layer by a polycarbonate filter having a pore size of 8 μm, and dried at room temperature overnight. It was swelled with a culture solution immediately before the use and set into a culture plate with 24 wells. As the tumor cells, highly metastatic clone B16FE7 derived from B16 melanoma was used. The cells were cultured for two days in the presence of 2 μCi/ml [$^3$H] thymidine. Immediately before the use, the cells were recovered by a trypsin solution and then suspended in a culture solution containing 1.0% of bovine albumin, whereupon the number of cells and the radioactivity of the [$^3$HI] thymidine incorporated, were determined.

Into the lower layer of the chemotaxicell, 20 μg/ml of human fibronectin was put, and into the upper layer, $5\times 10^4$ cells were put together with various concentrations of peptides, followed by culturing for 20 hours in a $CO_2$ incubator. After completion of the culturing, the cells remaining on the upper side of the filter were scraped off with a cotton swab and dissolved together with the cells migrated to the lower side, by a tissue solubilizer (manufactured by Amersham Company), and then the radioactivity was measured.

Figure 2:
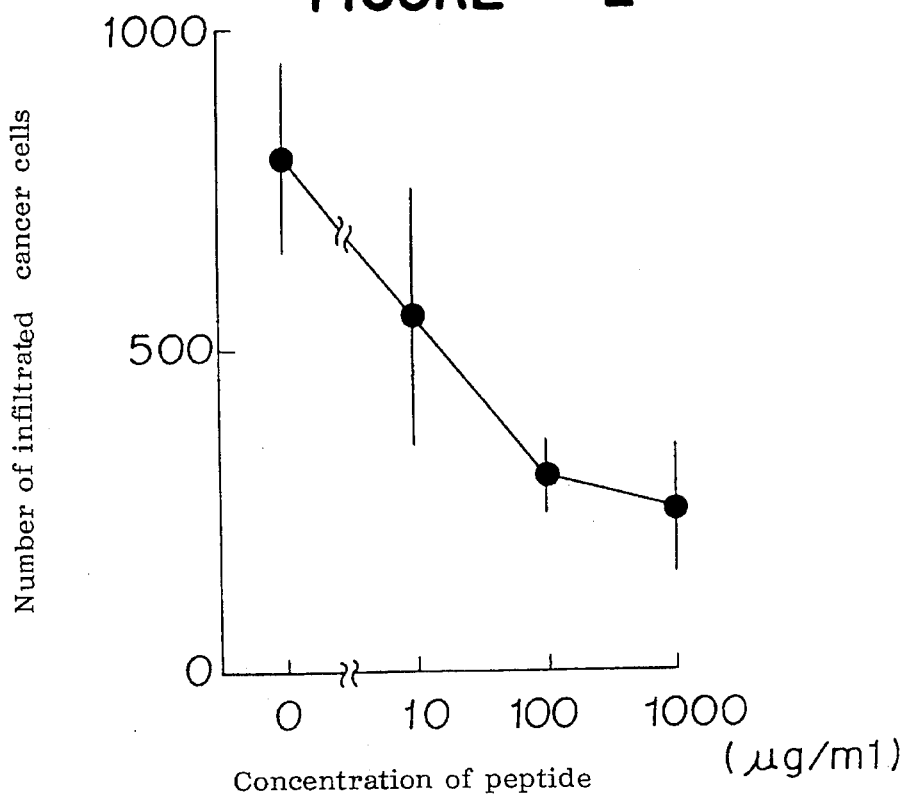
Figure 3:
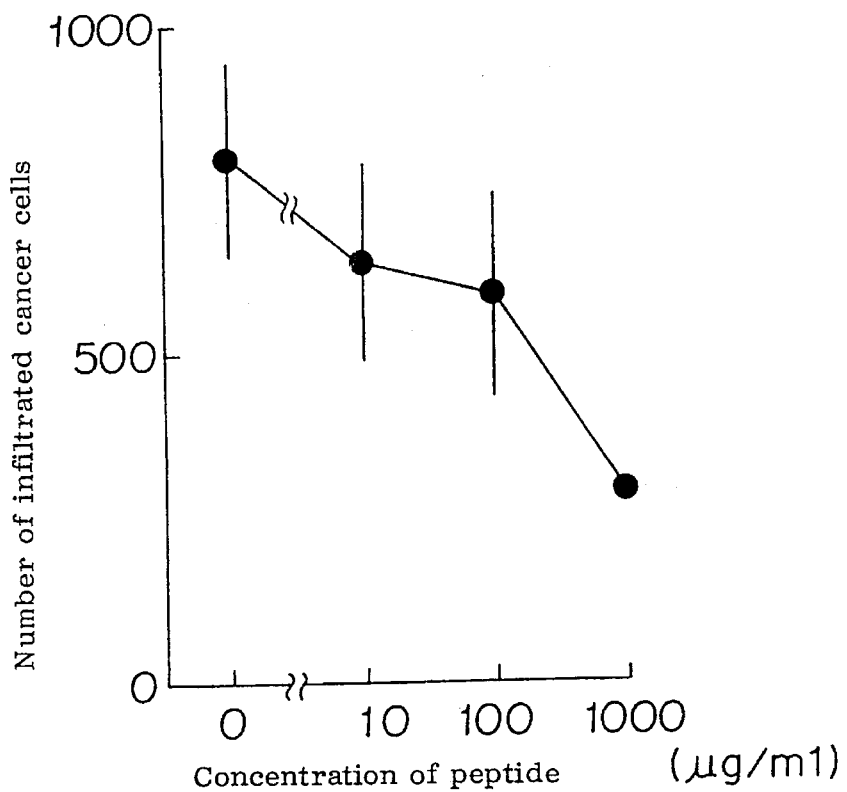

As the peptide, the following peptides were used, and the results are shown in FIGS. 1 to 3.

The peptide of the formula (7): FIG. 1

The peptide of the formula (6): FIG. 2

The peptide of the formula (13): FIG. 3

EXAMPLE C (Tumor cell metastasis-inhibiting activities of synthesized peptides)

With respect to the peptides prepared in Example A, the activities for inhibiting the metastasis of tumor cells were examined.

Highly metastatic mouse tumor cells B16FE7 in an amount of 1.2×10$^5$ cells (variable) per C 57BL/6j mouse (7 weeks old, female) and various concentrations of the synthesized peptides of the present invention were injected in the lateral vein of the mouse. Two weeks later, the mouse was killed, and the lung was extracted and the number of metastatic foci on the lung surface was counted under a dissecting microscope.

The results are shown in Tables 1 to 3 together with the type of the peptide and the number of tumor cells injected per mouse.

TABLE 1

Activities of the peptide of the formula (7) against cancer metastasis (Number of injected tumor cells: 1.2 × 10$^5$ cells per mouse)

| Amount of peptide (μg/mouse) | Number of metastatic foci on the lung surface | Average ± standard error |
| --- | --- | --- |
| 0 | 27, 30, 32, 66, 68, 72 | 40.2 ± 8.8 |
| 100 | 17, 20, 22, 27, 32, 44 | 27.0 ± 4.0 |
| 300 | 19, 21, 30, 31, 38, 39 | 29.7 ± 3.4 |

TABLE 2

Activities of the peptide of the formula (6) against cancer metastasis (Number of injected tumor cells: 1.2 × 10$^5$ cells per mouse)

| Amount of peptide (μg/mouse) | Number of metastatic foci on the lung surface | Average ± standard error |
| --- | --- | --- |
| 0 | 27, 30, 32, 66, 68, 72 | 49.2 ± 8.8 |
| 100 | 17, 20, 22, 27, 32, 44 | 27.0 ± 4.0 |
| 300 | 19, 21, 30, 31, 38, 39 | 29.7 ± 3.4 |

TABLE 3

Activities of the peptide of the formula (13) against cancer metastasis (Number of injected tumor cells: 1.2 × 10$^5$ cells per mouse)

| Amount of peptide (μg/mouse) | Number of metastatic foci on the lung surface | Average ± standard error |
| --- | --- | --- |
| 0 | 49, 58, 63, 99, 145, 155, 227, 236 | 129.0 ± 26.3 |
| 300 | 17, 27, 46, 53, 74, 80 | 49.5 ± 10.2 |

REFERENCE EXAMPLE (Preparation of the peptide of the formula (14))

Preparation of the peptide of the formula (14) (Ala-Glu-Asp-Gly-Asp-Ala-Lys-Thr-Asp-Glx-Ala-Glx-Lys-Ala-Glu-Gly-Ala-Gly-Asp-Ala-Lys)

In the same manner as in Example A, the above-identified peptide was prepared by an automatic synthesizer model 9050, manufactured by Milligen Company.

Then, this product was purified by high performance liquid chromatography (HPLC) under the following conditions.

Column: C18 column, manufactured by Waters Company, μBondasphere C18 column (1.9×15 cm, particle diameter: 5 μm)

Eluate A: Water containing 0.1% trifluoroacetic acid

Eluate B: Acetonitrile containing 0.1% trifluoroacetic acid

Flow rate: 10 ml/min Eluate B was eluted under a linear concentration gradient from 0 to 60% over a period of from 0 to 30 minutes.

The eluted peptide was recovered and freeze-dried.

Analysis: completely hydrolyzed in 6N hydrochloric acid at 110° C. for 24 hours under vacuum and then subjected to an amino acid analysis.

Further, a part thereof was analyzed by a HPLC apparatus using a reversed column, μBondasphere C18 column (0.39× 15 cm), manufactured by Waters Company, whereby no impurities other than the peptide, were detected. Thus, the purity of the synthesized peptide was at least 99%.

EXAMPLE D (Preparation of complexes of the peptide of the formula (14))

Example D-1

Preparation of a Complex of the Peptide of the Formula (14)-serum Albumin

The peptide of the formula (14) prepared in the Reference Example was bonded to mouse serum albumin by a condensation reaction by means of a water-soluble carbodiimide.

100 mg of the peptide of the formula (14) prepared in the Reference Example and 100 mg of mouse serum albumin were dissolved in 10 cm$^3$ of distilled water, and the pH was adjusted to 8.5 with a 1N sodium hydroxide solution. To this solution, 1 cm$^3$ of 100 mg/cm$^3$ of a 1-ethyl-3-(3-dimethylaminopropyl) carbodiimide solution was added, and the mixture was reacted at 37° C. for two hours and then at 4° C. for 12 hours. A 1M glycin solution was added to terminate the reaction, and then dialysis was conducted against 5,000 cm$^3$ of distilled water. The obtained solution was subjected to high performance liquid chromatography (reversed phase chromatography) to purify the complex.

The purification conditions were the same as in the Reference Example, and the peptide-mouse serum albumin complex was eluted far after the non-reacted peptide or a complex of the peptide itself, whereby it was possible to completely separate it from the rest.

The eluted complex was subjected to freeze-drying. The amount of the obtained complex was 90 mg. The purified complex was analyzed by SDS-polyacrylamide electrophoresis, whereby no impurities other than the complex were detected. The molecular weight of the mouse serum albumin was about 67,000, but by the above bonding reaction, the peptide was bonded thereto, and the average molecular weight was changed to 74,000. This indicates that about 2.5 molecules of the peptide were bonded per molecule of the mouse serum albumin.

EXAMPLE D-2

Preparation of a [$^{14}$C]-labeled complex

The complex of the peptide of the formula (14)-serum albumin prepared in Example D-1 was labeled with [14C] by a reduction ethylation reaction (Jentoft & Dearborn, Methods in Enzymology, 91, 570, (1983)).

The peptide-serum albumin complex prepared in Example D-1 was dissolved in a 10 mM phosphate buffer solution containing 0.15M sodium chloride (PBS) to have a concentration of 8 mg/cm$^3$, and to 0.5 cm$^3$ thereof, 0.25 cm$^3$ of 0.1M NaBH³CN was added, and 10 μCi of [¹⁴C] formaldehyde (manufactured by Amersham Company; 477 MBq/cm$^3$) was further added. The mixture was reacted at 4° C. for 20 hours. After completion of the reaction, PBS was added, and demineralization and concentration were repeated by means of Centricon 10 (manufactured by Amicon Corporation). In the labeled product, 1,735 cpm/μg of [¹⁴C] was taken in (cpm: count/minute).

The labeled product was analyzed by SDS-PAGE, whereby it was found to behave in the same manner as the non-labeled complex, and it exhibited the same level of tumor cell invasion-inhibiting activities.

EXAMPLE D-3

Preparation of a peptide-IgG Complex

The peptide of the formula (14) prepared in the Reference Example was bonded to mouse IgG by a condensation reaction by means of a water-soluble carbodiimide.

20 mg of the peptide of the formula (14) prepared in the Reference Example and 20 mg of mouse IgG were dissolved in 1 cm$^3$ of distilled water, and the pH was adjusted to 8.5 with a 1N sodium hydroxide aqueous solution. To this solution, 0.1 cm$^3$ of 100 mg/cm$^3$ of a 1-ethyl-3-(3-dimethylaminopropyl) carbodiimide solution was added, and the mixture was reacted at 37° C. for two hours and then at 4° C. for 12 hours. The reaction was terminated by an addition of a 1M glycin solution, and then dialysis was conducted against 3,000 cm$^3$ of distilled water, followed by freeze-drying to obtain 15 mg of a complex.

EXAMPLE E (Tumor cell invasion-inhibiting activities and metastasis-inhibiting activities of peptide complexes)

EXAMPLE E-1

Measurement of Tumor Cell Invasion-inhibiting Activities of the Peptide-serum Albumin Complex The activities for inhibiting invasion of tumor cells were examined with respect to the peptide-serum albumin complex prepared in Example D-1. The evaluation method was in accordance with the method of Albini et al. of Example B, and this peptide complex was used instead of the peptide in Example B.

Figure 4:
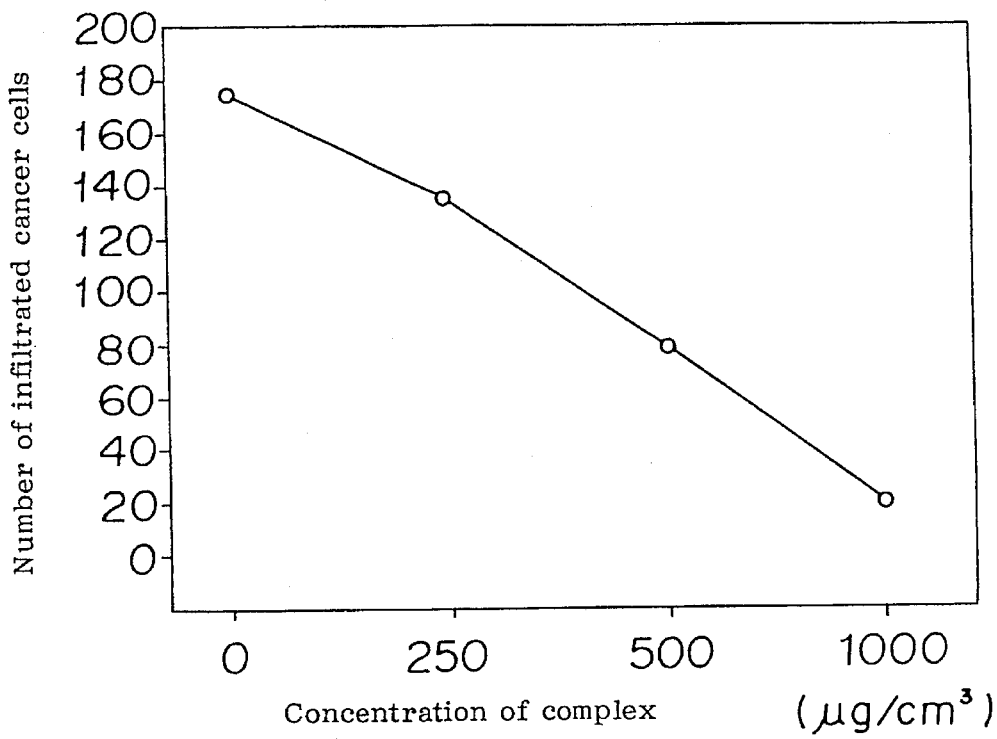

The results are shown in FIG. 4. It is evident that invasion of tumor cells was inhibited significantly by this complex.

EXAMPLE E-2

Measurement of the Kinetics of the Peptide in Blood and the Peptide-serum Albumin Complex The kinetics in blood of the peptide of the formula (14) prepared in the Reference Example and the [¹⁴C]-labeled complex prepared in Example D-2 were studied.

To the vein of the tail of a C57BL/6j mouse (8 weeks old, female), 1,000 μg/0.2 cm$^3$ of the peptide or 100 μg/0.2 cm$^3$ of the labeled complex was injected. Upon expiration of a predetermined period of time, the carotid artery was cut for blood sampling. To quantitatively analyze the amount of the peptide in blood, to 1 cm$^3$ of the sampled blood, the same amount of 10% trifluoroacetic acid was added, followed by centrifugal separation at a speed of 10,000 rpm to precipitate the denatured protein, and the supernatant was recovered. To this precipitate, 1.5 cm$^3$ of 10% trifluoroacetic acid was added and thoroughly stirred, followed by centrifugal separation, whereupon the supernatant was recovered and combined with the supernatant previously obtained. The combined supernatant was subjected to freeze-drying. To the obtained freeze-dried product, 0.2 cm$^3$ of distilled water was added, and the quantitative analysis was conducted by reversed phase (C18) chromatography. The quantitative analysis was conducted based on the quantitative curve obtained with a standard product (the peptide prepared in the Reference Example and quantitatively analyzed by an amino acid analysis).

To quantitatively analyze the [¹⁴C]-labeled complex, 2.5 cm$^3$ of a tissue solubilizer (NCA, Amersham Company) was added to 0.2 cm$^3$ of the sampled blood, followed by heating at 50° C. for two hours to solubilize the blood. Then, 0.2 cm$^3$ of a 30% hydrogen-peroxide aqueous solution was added thereto, followed by heating at 50° C. for a further one hour to decolor the solution. The solution was cooled to room temperature and then 15 cm$^3$ of a liquid scintillation cocktail was added, and the radiation of [¹⁴C] was measured by a liquid scintillation counter.

Figure 5:
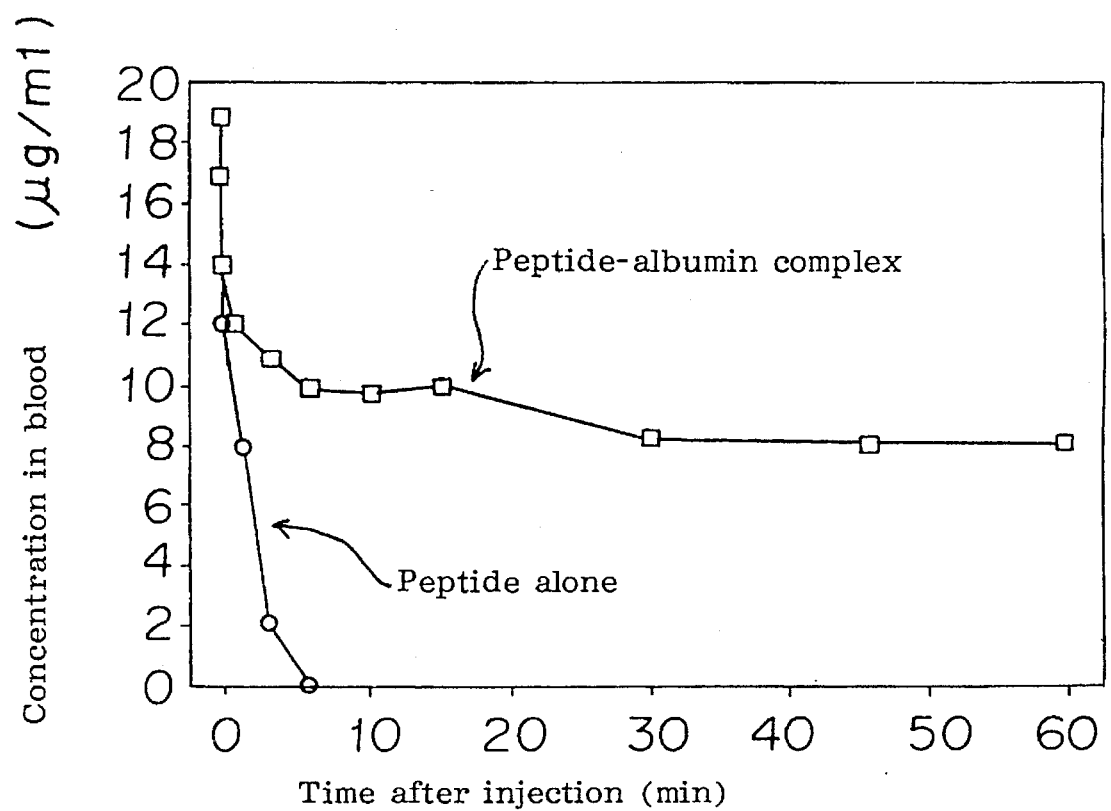
FIG. 5 is a graph showing the results obtained by measuring the kinetics of the peptide in blood and the peptide complex of the present invention in Example E-4 given hereinafter.

As a result, as shown in FIG. 5, the half life in blood of the peptide was about 20 seconds, and it disappeared in blood in about 3 minutes, whereas the curve of disappearance in blood of the peptide-serum albumin complex showed two phases, and it was found that even upon expiration of 60 minutes, the complex still remained at a level of 40%. Since the half life in blood of the peptide-albumin complex was prolonged substantially, the continuation of the activities can be expected.

EXAMPLE E-3

Cancer Metastasis-inhibiting Activities of Peptide Complexes

With respect to the peptide-serum albumin complex prepared in Example D-1 and the peptide-IgG complex prepared in Example D-3, the activities for inhibiting metastasis of tumor cells were examined by the method of Example C. The results are shown in Tables 4 and 5.

TABLE 4

Activities of the complex of the peptide of the formula (14)-serum albumin against cancer metastasis

| Amount of complex (μg/mouse) | Number of metastatic foci on the lung surface | Average ± standard error |
|---|---|---|
| 0 | 54, 56, 105, 121, 129, 248, 310, 387 | 176.3 ± 43.7 |
| 220 | 49, 54, 77, 75, 84, 103, 142, 157 | 91.8 ± 14.0 |
| 670 | 50, 57, 58, 59, 61, 62, 158 | 72.1 ± 14.4 |
| 2000 | 3, 5, 13, 18, 29, 36, 58 | 23.1 ± 7.4 |

TABLE 5

Activities of the complex of the peptide of the formula (14)-IgG against cancer metastasis

| Amount of complex (μg/mouse) | Number of metastatic foci on the lung surface | Average standard error |
|---|---|---|
| 0 | 7, 10, 14, 21, 40 | 18.4 ± 6.6 |
| 500 | 6, 10, 10, 18, 20 | 12.8 ± 3.5 |
| 1000 | 5, 5, 6, 6, 7 | 5.8 ± 0.4 |

EXAMPLE F (Preparation of peptide-serum albumin complexes)

EXAMPLE F-1

Preparation of a Complex (i) of the Peptide of the Formula (7)-serum Albumin

The peptide of the formula (7) prepared in Example A-1 was bonded to mouse serum albumin by the condensation reaction by means of a water-soluble carbodiimide in the same manner as in Example D-1. The amount of the obtained complex was 90 mg.

The purified complex was analyzed by SDS-polyacrylamide electrophoresis, whereby no impurities other than the complex were detected. The molecular weight of the mouse serum albumin was 66,000, and by the above bonding reaction, the peptide was bonded, whereby the average molecular weight was changed to 69,000. This indicates that an average of 2.5 molecules of the peptide of the formula (7) were bonded per molecule of the mouse serum albumin.

EXAMPLE F-2

Preparation of a Complex (ii) of the Peptide of the Formula (6)-serum Albumin

The peptide of the formula (6) prepared in Example A-2 was bonded to mouse serum albumin by the condensation reaction by means of a water-soluble carbodiimide in the same manner as in Example F-1. The amount of the complex of the peptide of the formula (6)-albumin was 81 mg, and an average of 3.1 molecules of the peptide of the formula (6) were bonded per molecule of albumin.

EXAMPLE F-3

Preparation of a Complex (iii) of the Peptide of the Formula (9)-serum Albumin

A complex was prepared by treating the peptide of the formula (9) prepared in Example A-4 by a water-soluble carbodiimide in the same manner as in Example F-1. The amount of the complex was 84 mg, and an average of 2.8 molecules of the peptide of the formula (9) were bonded per molecule of albumin.

EXAMPLE F-4

Preparation of a Complex (iv) of the Peptide of the Formula (13)-serum Albumin

The peptide of the formula (3) prepared in Example A-3 was bonded to albumin by a water-soluble carbodiimide method in the same manner as in Example F-1. The amount was 91 mg. An average of 5.2 molecules of the peptide of the formula (13) were bonded per molecule of albumin.

EXAMPLE G (Tumor cell invasion-inhibiting activities of the peptide complexes)

Measurements of Tumor Cell Invasion-inhibiting Activities of the Peptide-serum Albumin Complexes (i) to (iv)

With respect to the peptide-serum albumin complexes prepared in Examples F-1 to F-4, activities for inhibiting invasion of tumor cells were investigated. The evaluation was conducted in accordance with the method of Albini et al. of Example B by using these peptide complexes instead of the peptide used in Example B. The results are shown in Table 6.

TABLE 6

Activities of peptide complexes against cancer metastasis

| Complex | Amount of complex (μg/ml) | Number of invaded tumor cells | Inhibition (%) |
| --- | --- | --- | --- |
| — | 0 | 1342 | — |
| Complex (i) | 500 | 421 | 68.7 |
| Complex (ii) | 500 | 342 | 74.5 |
| Complex (iii) | 500 | 481 | 64.2 |
| Complex (iv) | 500 | 290 | 78.4 |

EXAMPLE H (Cancer metastasis-inhibiting activities of peptide complexes)

Cancer Metastasis-inhibiting Activities of the Peptide-serum Albumin Complexes (i) to (iv)

With respect to the peptide complexes prepared in Examples F-1 to F-4, the activities for inhibiting metastasis of tumor cells were examined in accordance with the method of Example C. The results are shown in Table 7.

TABLE 7

Activities of the peptide-serum albumin complexes (i) to (iv) against cancer metastasis

| Complex | Amount of complex (μg/ml) | Number of metastatic foci on the lung surface | Average ± standard error |
| --- | --- | --- | --- |
| — | 0 | 67, 89, 109, 132, 176, 187 | 126.7 ± 47.7 |
| Complex (i) | 1000 | 18, 19, 23, 35, 41, 58 | 32.3 ± 15.6 |
| Complex (ii) | 1000 | 22, 24, 31, 42, 44, 61 | 37.3 ± 14.7 |
| Complex (iii) | 1000 | 11, 13, 21, 39, 46, 51 | 30.2 ± 17.4 |
| Complex (iv) | 1000 | 9, 19, 25, 27, 31, 45 | 26.0 ± 12.0 |

EXAMPLE I (Preparation of complexes of the peptide of the formula (14))

EXAMPLE I-1

Preparation of a Peptide-chondroitin Sulfate Complex

The peptide of the formula (14) prepared in the Reference Example was bonded to chondroitin sulfate derived from a bovine trachea, by a condensation reaction by means of a water-soluble carbodiimide.

100 mg of chondroitin sulfate was dissolved in 2 cm$^3$ of distilled water. To this solution, 1-ethyl-3-(3-dimethylaminopropyl) carbodiimide was added so that the final concentration would be 70 mM, and the mixture was reacted at room temperature for 30 minutes. To this reaction solution, 10 mg of the peptide of the formula (14) was added, and the mixture was reacted at room temperature for further 20 hours. To the reaction product, 3 times of methanol was added to precipitate the complex.

The precipitate was recovered by centrifugal separation, and distilled water was added thereto to dissolve the precipitate. Then, dialysis was repeated five times against 5,000 cm of distilled water. Obtained complex was subjected to high performance liquid chromatography (gel permeation), whereby it was confirmed that no unreacted peptide of the formula (14) remained. The amount of the complex thereby obtained was 79 mg. A part thereof was subjected to an amino acid analysis, whereby it was found that 63 μg of the peptide was bonded per mg of the complex.

EXAMPLE I-2

Preparation of a Peptide-hyaluronic Acid Complex

The peptide of the formula (14) prepared in Reference Example 1 was bonded to hyaluronic acid derived from bovine trachea, by a condensation reaction by means of a water-soluble carbodiimide.

To 1 $cm^3$ of a 10 mM phosphate buffer solution (pH7.4), 10 mg of hyaluronic acid was dissolved, and 1-ethyl-3-(3-dimethylaminopropyl) carbodiimide was added thereto so that the final concentration would be 70 mM, and the mixture was reacted at room temperature for 30 minutes. To the reaction product, 10 mg of the peptide of the formula (14) was added, and the mixture was reacted at room temperature for further 20 hours. To the reaction mixture, 3 times of methanol was added to precipitate a complex.

The precipitate was recovered by centrifugal separation, and it was dissolved in distilled water. Then, dialysis was repeated five times against 5,000 $cm^3$ of distilled water. The obtained complex was subjected to high performance liquid chromatography (gel permeation), whereby it was confirmed that no unreacted peptide of the formula (14) remained. The amount of the obtained complex was 6.4 mg. A part thereof was subjected to an amino acid analysis, whereby it was found that 190 μg of the peptide was bonded per mg of the complex.

EXAMPLE J (Cancer metastasis-inhibiting activities of a peptide complex)

Test for the Cancer Metastasis-inhibiting Activities of the Peptide-chondroitin Sulfate Complex With respect to the complex of the peptide of the formula (14)-chondroitin sulfate prepared in Example I-1, the activities for inhibiting metastasis of tumor cells were examined in accordance with the method of Example C. The results are shown in Table 8.

TABLE 8

Activities of the peptide-chondroitin sulfate complex against cancer metastasis

| Amount of peptide (μg/ mouse) | Number of metastatic foci on the lung surface | Average ± standard error |
|---|---|---|
| 0 | 35, 142, 164, 190, 342 | 174.6 ± 49.5 |
| 10 | 16, 38, 43, 62, 68 | 45.4 ± 9.2 |

---

We claim:

1. A peptide or acid addition salt thereof, wherein said peptide has tumor cell invasion-inhibiting activity and has an amino acid sequence of any one of the following formulas (1) to (13);
  (1) Ala-Glx-Lys-Ala-Glx-Gly
  (2) Ala-Glx-Lys-Ala-Glx-Gly-Ala
  (3) Ala-Glx-Lys-Ala-Glx-Gly-Ala-Gly
  (4) Ala-Glx-Lys-Ala-Glx-Gly-Ala-Gly-Asx
  (5) Ala-Glx-Lys-Ala-Glx-Gly-Ala-Gly-Asx-Ala
  (6) Ala-Glx-Lys-Ala-Glx-Gly-Ala-Gly-Asx-Ala-Lys
  (7) Asx-Ala-Lys-Thr-Asx-Glx-Ala-Glx-Lys-Ala-Glx-Gly
  (8) Ala-Lys-Thr-Asx-Glx-Ala-Glx-Lys-Ala-Glx-Gly
  (9) Lys-Thr-Asx-Glx-Ala-Glx-Lys-Ala-Glx-Gly
  (10) Thr-Asx-Glx-Ala-Glx-Lys-Ala-Glx-Gly
  (11) Asx-Glx-Ala-Glx-Lys-Ala-Glx-Gly
  (12) Glx-Ala-Glx-Lys-Ala-Glx-Gly
  (13) Asx-Glx-Ala-Glx-Lys-Ala
wherein Glx is Gly or Gln, and Asx is Asn or Asp.

2. A cancer metastasis inhibitor, comprising a peptide which has tumor cell invasion-inhibiting activity and has an amino acid sequence of any one of the following formulas (1) to (13):
  (1) Ala-Glx-Lys-Ala-Glx-Gly
  (2) Ala-Glx-Lys-Ala-Glx-Gly-Ala
  (3) Ala-Glx-Lys-Ala-Glx-Gly-Ala-Gly
  (4) Ala-Glx-Lys-Ala-Glx-Gly-Ala-Gly-Asx
  (5) Ala-Glx-Lys-Ala-Glx-Gly-Ala-Gly-Asx-Ala
  (6) Ala-Glx-Lys-Ala-Glx-Gly-Ala-Gly-Asx-Ala-Lys
  (7) Asx-Ala-Lys-Thr-Asx-Glx-Ala-Glx-Lys-Ala-Glx-Gly
  (8) Ala-Lys-Thr-Asx-Glx-Ala-Glx-Lys-Ala-Glx-Gly
  (9) Lys-Thr-Asx-Glx-Ala-Glx-Lys-Ala-Glx-Gly
  (10) Thr-Asx-Glx-Ala-Glx-Lys-Ala-Glx-Gly
  (11) Asx-Glx-Ala-Glx-Lys-Ala-Glx-Gly
  (12) Glx-Ala-Glx-Lys-Ala-Glx-Gly
  (13) Asx-Glx-Ala-Glx-Lys-Ala.

3. A peptide complex comprising a peptide having tumor cell invasion-inhibiting activity supported on a substantially non-toxic polymer carrier wherein said peptide having tumor cell invasion-inhibiting activity is a peptide having an amino acid sequence of any one of the following formulas (1) to (14):
  (1) Ala-Glx-Lys-Ala-Glx-Gly
  (2) Ala-Glx-Lys-Ala-Glx-Gly-Ala
  (3) Ala-Glx-Lys-Ala-Glx-Gly-Ala-Gly
  (4) Ala-Glx-Lys-Ala-Glx-Gly-Ala-Gly-Asx
  (5) Ala-Glx-Lys-Ala-Glx-Gly-Ala-Gly-Asx-Ala
  (6) Ala-Glx-Lys-Ala-Glx-Gly-Ala-Gly-Asx-Ala-Lys
  (7) Asx-Ala-Lys-Thr-Asx-Glx-Ala-Glx-Lys-Ala-Glx-Gly
  (8) Ala-Lys-Thr-Asx-Glx-Ala-Glx-Lys-Ala-Glx-Gly
  (9) Lys-Thr-Asx-Glx-Ala-Glx-Lys-Ala-Glx-Gly
  (10) Thr-Asx-Glx-Ala-Glx-Lys-Ala-Glx-Gly
  (11) Asx-Glx-Ala-Glx-Lys-Ala-Glx-Gly
  (12) Glx-Ala-Glx-Lys-Ala-Glx-Gly
  (13) Asx-Glx-Ala-Glx-Lys-Ala
  (14) Ala-Glu-Asp-Gly-Asp-Ala-Lys-Thr-Asp-Glx-Ala-Glx-Lys-Ala-Glu-Gly-Ala-Gly-Asp-Ala-Lys
wherein Glx is Gly or Gln, and Asx is Asn or Asp.

4. The peptide complex according to claim 3, wherein said polymer carrier is a protein.

5. The peptide complex according to claim 4, wherein the protein is albumin or globulin.

6. The peptide complex according to claim 3, wherein said polymer carrier is chondroitin sulfate or hyaluronic acid.

7. The peptide complex according to claim 3, wherein said peptide is chemically banded to said polymer carrier by a carbodiimide condensation method.

8. A peptide selected from the group consisting of:
  Asp-Ala-Lys-Thr-Asp-Gln-Ala-Glu-Lys-Ala-Glu-Gly,
  Ala-Glu-Lys-Ala-Glu-Gly-Ala-Gly-Asp-Ala-Lys, and
  Asp-Gln-Ala-Glu-Lys-Ala.

9. A peptide complex having a peptide selected from the group consisting of:
  Ala-Glu-Asp-Gly-Asp-Ala-Lys-Thr-Asp-Glx-Ala-Glx-Lys-Ala-Glu-Gly-Ala-Gly-Asp-Ala-Lys,
  Asp-Ala-Lys-Thr-Asp-Gln-Ala-Glu-Lys-Ala-Glu-Gly,
  Ala-Glu-Lys-Ala-Glu-Gly-Ala-Gly-Asp-Ala-Lys,
  Asp-Gln-Ala-Glu-Lys-Ala and
  Lys-Thr-Asp-Gln-Ala-Glu-Lys-Ala-Glu-Gly
wherein Glx is Glu or Gln;
supported to a substantially non-toxic polymer carrier.

* * * * *